US011959905B2

(12) United States Patent
Lindsay et al.

(10) Patent No.: US 11,959,905 B2
(45) Date of Patent: *Apr. 16, 2024

(54) SYSTEM AND METHOD FOR SINGLE MOLECULE DETECTION

(71) Applicant: ARIZONA BOARD OF REGENTS on behalf of ARIZONA STATE UNIVERSITY, Scottsdale, AZ (US)

(72) Inventors: Stuart Lindsay, Phoenix, AZ (US); Peiming Zhang, Gilbert, AZ (US); Yanan Zhao, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/178,130

(22) Filed: Mar. 3, 2023

(65) Prior Publication Data
US 2023/0243807 A1 Aug. 3, 2023

Related U.S. Application Data

(63) Continuation of application No. 16/917,474, filed on Jun. 30, 2020, now Pat. No. 11,630,098, which is a
(Continued)

(51) Int. Cl.
*G01N 27/327* (2006.01)
*G01N 33/487* (2006.01)
(52) U.S. Cl.
CPC ..... *G01N 33/48721* (2013.01); *G01N 27/3276* (2013.01); *G01N 27/3278* (2013.01)

(58) Field of Classification Search
CPC ... G01N 33/48721; G01N 27/32–3272; G01N 27/3275–3278; G01N 27/4145
See application file for complete search history.

(56) References Cited

U.S. PATENT DOCUMENTS 6,391,558 B1   5/2002   Henkens et al.
6,824,974 B2   11/2004  Pisharody et al.
(Continued)

FOREIGN PATENT DOCUMENTS

WO   WO 2015/130781 A1   9/2015
WO   WO 2015/131073 A1   9/2015
WO   WO 2015/161119 A1   10/2015

OTHER PUBLICATIONS

Amdursky, N. et al., "Electronic Transport via Proteins," Adv Mater. 26(42): pp. 7142-7161 (2014).
(Continued)

*Primary Examiner* — Alexander S Noguerola
(74) *Attorney, Agent, or Firm* — Casimir Jones, S.C.; Peter J. Schlueter

(57) ABSTRACT

A single molecule sensing or detecting device includes a first electrode and a second electrode separated from the first electrode by a gap. The first electrode and the second electrode have an opening formed therethrough. At least one of the first electrode and the second electrode is functionalized with a recognition molecule. The recognition molecule has an effective length LI and is configured to selectively bind to a target molecule having an effective length L2. The size of the gap is configured to be greater than L2, but less than or equal to the sum of LI and L2.

17 Claims, 14 Drawing Sheets

Related U.S. Application Data continuation of application No. 16/537,232, filed on Aug. 9, 2019, now abandoned, which is a continuation of application No. 15/375,901, filed on Dec. 12, 2016, now Pat. No. 10,379,102.

(60) Provisional application No. 62/266,282, filed on Dec. 11, 2015.

(56) References Cited

U.S. PATENT DOCUMENTS

| | | |
|---|---|---|
| 7,785,785 B2 | 8/2010 | Pourmand et al. |
| 8,628,649 B2 | 1/2014 | Lindsay et al. |
| 8,753,893 B2 | 6/2014 | Liu et al. |
| 8,961,757 B2 | 2/2015 | Nuckolls et al. |
| 8,968,540 B2 | 3/2015 | Reinhart et al. |
| 9,140,682 B2 | 9/2015 | Lindsay et al. |
| 9,274,430 B2 | 3/2016 | Gyarfas et al. |
| 9,395,352 B2 | 7/2016 | Lindsay et al. |
| 9,593,372 B2 | 3/2017 | Lindsay et al. |
| 9,766,248 B2 | 9/2017 | Lindsay et al. |
| 9,810,681 B2 | 11/2017 | Lindsay et al. |
| 10,036,064 B2 | 7/2018 | Merriman et al. |
| 10,379,102 B2 | 9/2019 | Lindsay et al. |
| 11,630,098 B2 * | 4/2023 | Lindsay ........... G01N 33/48721 204/451 |
| 2003/0064390 A1 | 4/2003 | Schuleain et al. |
| 2006/0154489 A1 | 7/2006 | Tornow et al. |
| 2009/0017571 A1 | 1/2009 | Nuckolis et al. |
| 2009/0295372 A1 | 12/2009 | Krstic et al. |
| 2010/0084276 A1 | 4/2010 | Lindsay et al. |
| 2011/0166034 A1 | 7/2011 | Kwong et al. |
| 2012/0258870 A1 | 10/2012 | Schwartz et al. |
| 2013/0302901 A1 | 11/2013 | Lindsay et al. |
| 2015/0010935 A1 | 1/2015 | Lindsay et al. |
| 2015/0142327 A1 | 5/2015 | Ashcroft et al. |
| 2015/0144506 A1 | 5/2015 | Lindsay et al. |
| 2016/0018384 A1 | 1/2016 | Lindsay et al. |
| 2016/0025702 A1 | 1/2016 | Lindsay et al. |
| 2016/0108002 A1 | 4/2016 | Zhang et al. |
| 2016/0177383 A1 | 6/2016 | Ashcroft et al. |
| 2016/0194698 A1 | 7/2016 | Lindsay |
| 2016/0258925 A1 | 9/2016 | Gyarfas et al. |
| 2016/0280723 A1 | 9/2016 | Zhang et al. |
| 2017/0003245 A1 | 1/2017 | Lindsay et al. |
| 2017/0016852 A1 | 1/2017 | Lindsay et al. |
| 2017/0038369 A1 | 2/2017 | Lindsay et al. |
| 2017/0067902 A1 | 3/2017 | Zhang et al. |
| 2017/0137389 A1 | 5/2017 | Zhang et al. |
| 2017/0204066 A1 | 7/2017 | Lindsay et al. |
| 2017/0343558 A1 | 11/2017 | Lindsay et al. |
| 2019/0004003 A1 | 1/2019 | Merriman et al. |

OTHER PUBLICATIONS

Arielly, R. et al., "Real-Time Detection of Redox Events in Molecular Junctions," J Am Chem Soc. 136(6): pp. 2674-2680 (2014).
Artés, J. M. et al. "Transistor-like Behavior of Single Metalloprotein Junctions" Nano Lett., 2012, 12(6), pp. 2679-2684 (publication date (Web): Oct. 5, 2011).
Artes, J. M. et al., "Conductance Switching in Single Wired Redox Proteins," Small 10(13): pp. 2537-2541 (2014).
Bogomolny, E. et al., "Structure of Wave Functions of Pseudointegrable Billiards," Phys Rev Lett. 92: pp. 244102-1-244102-4 (2004).
Bogomolny, E. et al., "Models of intermediate spectral statistics," Phys Rev E. 59: pp. R1315-R1318 (1999).
Beratan, D. N. et al., "Charge Transfer in Dynamical Biosytems, or The Treachery of (Static) Images," Acc. Chem Res. 48(2): pp. 474-481 (2015).
Bertazzon, A. et al., "Scanning tunneling microscopy imaging of Torpedo acetylcholine receptor," Proc Natl Acad Sci. USA 89(20): pp. 9632-9639 (1992).

Chang, S. et al., "Gap Distance and Interactions in a Molecular Tunnel Junction," J Am Chem Soc. 133(36): pp. 14267-14269 (2011).
Chang, S. et al., "Palladium electrodes for molecular tunnel junctions," Nanotechnology 23(42): pp. 1-5 (2012).
Chen et al., "A protein transistor made of an antibody molecule and two gold nanoparticles," Nature Nanotechnology 2012, (7): 197-203.
Choi, Y. et al. "Site-specific inhibition of integrin alpha v beta 3-vitronectin association by a ser-asp-val sequence through an Arg-Gly-Asp-binding site of the integrin." Proteomics, vol. 10, Issue 1, No. 1 Jan. 2010, pp. 72-80 (First published Oct. 30, 2009).
Cui, X. D. et al. "Reproducible Measurement of Single-Molecule Conductivity" Science, vol. 294, Issue 5542, pp. 571-574 (Oct. 19, 2001).
Dong, X. et al., "Alpha(v)beta(3) Integrin Crystal Structures and Their Functional Implications," Biochemistry 51(44): pp. 8814-8828 (2012).
Engel, G. S. et al., "Evidence for wavelike energy transfer through quantum coherence in photosynthetic systems," Nature 446(7137): pp. 782-786 (2007).
Fan, F. R. F. et al., "Electrochemical Detection of Single Molecules," Science 267: pp. 871-874 (1995).
Grdeń, M. et al., "Electrochemical behavior of palladium electrode: Oxidation, electrodissolution and ionic adsorption," Electrochimca Acta. 53: pp. 7583-7806 (2008).
Haiss, W. et al., "Thermal gating of the single molecule conductance of alkanedithiols," Faraday Discussions 131: pp. 253-264 (2006).
Hoffman, R., "An Extended Huckel Theory I. hydrocarbons," J Chem Phys. 39: pp. 1397-1412 (1963).
Im, J. et al., "Electronic single-molecule identification of carbohydrate isomers by recognition tunneling," Nat Commun. 7: pp. 1-7 (2016).
Karachaliou et al., "IgY technology: Methods for developing and evaluating avian immunoglubulins for the in vitro detection of biomolecules," World of Methodol 2021, 11(5): 243-262.
Kumar, K. S. et al., "Long-Range Tunneling Processes across Ferritin-Based Junctions," Adv Mater. 28(9): pp. 1824-1830 (2016).
Leatherbarrow, R. J. et al., "Structure of Immunoglobulin G by Scanning Tunneling Microscopy," J Mol Biol. 221(2): pp. 361-365 (1991).
Lindsay, S. et al., "Recognition tunneling," Nanotechnology 21(26): pp. 1-12 (2010).
Lloyd, S., "Quantum coherence in biological systems," Journal of Physics: Conference Series 302: pp. 1-5 (2011).
Luo, B. H. et al., "Structural Basis of Integrin Regulation and Signaling," Annu Rev Immunol. 25: pp. 619-647 (2007).
Malvankar, N. S. et al., "Tunable metallic-like conductivity in microbial nanowire networks," Nat. Nanotechnol. 6(9): pp. 573-579 (2011).
O'Boyle, N. M. et al., "Open Babel: An pen chemical toolbox," J Cheminform. 3: pp. 1-14 (2011).
Onuchic, J. N. et al., "Pathway Analysis of Protein Electron-Transfer Reactions," Annu. Rev. Biophys Biomol Struct. 21, pp. 349-377 (1992).
Palecek, E. et al., "Electrochemistry of Nonconjugated Proteins and Glycoproteins. Toward Sensors for Biomedicine and Glycomics," Chem Rev. 115(5): pp. 2045-2108 (2015).
Pang, P. et al. "Fixed-Gap Tunnel Junction for Reading DNA Nucleotides" ACS Nano, 2014, 8 (12), pp. 11994-12003 (Publication Date (Web): Nov. 7, 2014).
Polizzi, N. F. et al., "Physical constraints on charge transport through bacterial nanowires," Faraday Discussions 153, pp. 43-62 (2012).
Roxin et al., "Flexible or fixed: a comparative review of linear and cyclic cancer-targeting peptides." Future Meds. Chem. 2012, 4(12): 1601-1618.
Sancey, L. et al., "Clustering and Internalization of Integrin alphavbeta3 With a Tetrameric RGD-synthetic Peptide," Mol Ther. 17(5): pp. 837-843 (2009).
Simmons, J. G., "Generalized Formula for the Electric Tunnel Effect between Similar Electrodes Separated by a Thin Insulating Film," J Appl Phys. 34(6): pp. 1793-1803 (1963).

(56) References Cited

OTHER PUBLICATIONS

Stuchebrukhov, A. A., "Towards AB Initio Theory of Long-Distance Electron Tunneling in Proteins: Tunneling Currents Approach," Adv Chem Phys. 118: pp. 1-44 (2001).
Thomson, N. H. et al., "Molecular images of cereal proteins by STM," Ultramicroscopy 42-44 (Part B): pp. 1204-1213 (1992).
U.S. Appl. No. 62/184,776, filed Jun. 25, 2015.
Vattay, G. et al., "Quantum criticality at the origin of life," Journal of Physics: Conference Series 626: pp. 1-10 (2015).
Xiao, X. "Conductance Titration of Single-Peptide Molecules" J. Am. Chem. Soc. 2004, 126(17), pp. 5370-5371 (Publication Date (Web): Apr. 9, 2004).
Xiong, J. P. et al., "Crystal structure of the extracellular segment of integrin alpha Vbeta3 in complex with an Arg-Gly-Asp ligand," Science 296(5565): pp. 151-155 (2002).
Zhang, Y. et al., "Biological charge transfer via flickering resonance," Proc Natl Acad Sci. USA 111(28): pp. 10049-10054 (2014).
Zwolak, M. et al. "Electronic Signature of DNA Nucleotides via Transverse Transport" Nano Lett., 2005, 5(3), pp. 421-424 (Publication Date (Web): Feb. 12, 2005).

\* cited by examiner

Cyclo (Arg-Gly-Asp-D-Phe-Cys)
C(RGDfC)

SYSTEM AND METHOD FOR SINGLE MOLECULE DETECTION

CROSS-REFERENCE TO RELATED APPLICATIONS

This application is a continuation application of U.S. application Ser. No. 16/917,474, filed on Jun. 30, 2020, which is a continuation application of abandoned U.S. application Ser. No. 16/537,232, filed on Aug. 9, 2019, which is a continuation of U.S. application Ser. No. 15/375,901, filed on Dec. 12, 2016, now issued U.S. Pat. No. 10,379,102, which claims priority to and the benefits of U.S. Provisional Application No. 62/266,282, filed on Dec. 11, 2015, the contents of each of which are incorporated herein by reference in their entireties.

GOVERNMENT RIGHTS

This invention was made with government support under R01 HG006323, R01 HG009180 awarded by The National Institutes of Health. The government has certain rights in the invention.

ABSTRACT OF THE DISCLOSURE

The present disclosure presents systems, methods and devices for detecting single molecules by direct electronic measurement as they bind a cognate ligand. In some embodiments, high contrast signals are produced with no labels and sample concentrations in the femtomolar range.

BACKGROUND

Electron tunneling is, in principle, sensitive to the presence of a molecule in a tunnel gap formed between two closely spaced metal electrodes (Zwolak and Di Ventra 2005). However, in practice, tunnel gaps are quite insensitive to molecules that may be trapped between the electrodes because the inevitable hydrocarbon contamination of metal electrodes outside of an ultrahigh vacuum clean environment makes for a poor contact between the electrodes and the molecules.

It has been shown that reproducible and characteristic electrical signals can be obtained if molecules are chemically attached to each electrode forming a tunnel junction, by, for example, sulfur-metal bonds (Cui, Primak et al. 2001). Such permanent connections, however, do not make for versatile detectors because the molecule that bridges the gap must be modified at two sites with groups such as thiols. Pishrody et al. (Pishrody, Kunwar et al. 2004), proposed a solution in which electrode pairs were functionalized with molecules that did not, by themselves bridge the gap, but rather, formed a bridged structure when a target molecule became bound. This prior art is illustrated in FIG. 1. As shown, a first metal electrode 10 and a second metal electrode 12 are separated by a dielectric layer 16 with the electrode gap exposed at the edge of the layered device. A first recognition molecule 14a and a second recognition molecule 14b are chemically tethered to the electrodes by reactive groups 18. The molecules 14a and 14b are chosen so as to bind a target molecule 20 in such a way as to form a bridge across the gap between the electrodes when 20 binds both 14a and 14b. For example 14a and 14b may be composed of DNA oligomers chosen so have a sequence that, taken together, is complementary to a target DNA molecule 20. However, the simple device of FIG. 1 cannot be used as a single molecule detector, but rather, only as a system of a large number of such devices functionalized with many pairs of recognition molecules. In this way, the presence of certain molecules in a sample could be determined upon the measurement of current from many binding events.

U.S. publication no. 2010/0084276 (Lindsay et al.) discloses a device designed for sequencing polymers, such as DNA In some embodiments of this prior art, as illustrated in FIG. 2, two closely spaced electrodes 30, 31 are separated by dielectric layer 33. A nanopore 34 is then drilled through the structure and the exposed electrodes functionalized with recognition molecules 35. The molecules bind to a target analyte 36 at two separate sites. Thus, once an analyte molecule enters the pore, it brings together the recognition molecules to form a connected pathway across the gap. The approach of such embodiments differ from that of Pishrody at least because (a) the nanopore of Lindsay et al. permits only one analyte to enter at a time (e.g., so that a polymer may be sequenced, as each chemical unit of the polymer enters the pore and generates a characteristic signal), and (b) the gap between the electrodes 30 and 31 is sized such that that single molecule binding event generates a large current.

SUMMARY OF SOME OF THE EMBODIMENTS OF THE DISCLOSURE

It is an object of at least some of the embodiments of the present disclosure to provide a device that detects single molecule binding events by, for example, direct electronic detection of binding on only a single ligand, e.g., such as an antibody.

It is another object of at least some of the embodiments of the present disclosure to provide a device with a large exposed junction area configured for sensing low concentrations of samples rapidly. For example, in some embodiments, such junction areas correspond to junction gaps of from 0.1 to 100 nm, with the lateral extent of the junctions ranging from 1 nm to 100 microns. Sample concentrations can be as low as one femtomolar, or even lower. A large junction area can be configured to collect molecules from a large sample volume, so that the time for molecules to diffuse into the junction can be small. For example, for a junction of a few microns in lateral extent, and a gap size of 4 nm, exposure to a concentration of 100 femtomoles results in generation of signals in about 10 s.

In some embodiments, a device for sensing molecules in solution is provided which includes a first electrode and a second electrode separated from the first electrode by a gap. One or more of the electrodes are functionalized with one or more recognition molecules having an effective length L1 and configured to selectively bind to a target molecule having an effective length L2. The gap is configured to be greater than L2, but less than or equal to the total of L1 and L2.

In some embodiments, a method for sensing molecules in solution is provided, which includes providing the device according to some embodiments of the disclosure (e.g., the device embodiment above), applying a voltage bias across the electrodes, providing a sample to the device, monitoring current over time to determine at least one of the features thereof of a background and noise spikes, and determining, based on at least one of the background and noise spikes, determining one or more of: the presence of the target molecule; and a number of non-target molecules adsorbed on the first electrode and/or on the second electrode.

In some embodiments, a device includes a first electrode and a second electrode separated from the first electrode by a gap. At least one of the first electrode and the second electrode is functionalized with a recognition molecule. The recognition molecule has an effective length L1 and is configured to selectively bind to a target molecule having an effective length L2. The gap is configured to be greater than L2 in thickness, but less than or equal to the sum of L1 and L2.

In some embodiments, a method includes applying a voltage bias across a first electrode and a second electrode of a device. The second electrode is separated from the first electrode by a gap. At least one of the first electrode and the second electrode is functionalized with a recognition molecule that has an effective length L1 and is configured to selectively bind to a target molecule having an effective length L2. The method also includes contacting the first electrode and the second electrode with a solution containing the target molecule in a concentration from about 10 fM to about 10 pM. The method also includes monitoring current generated between the first electrode and the second electrode over time. The method also includes determining one or more of: based on a fluctuating portion of the current, the presence of the target molecule; and based on a background portion of the current, a number of non-target molecules adsorbed on the first electrode and on the second electrode.

DESCRIPTION OF THE PRESENT INVENTION IN ITS PREFERRED EMBODIMENT

Figure 1:
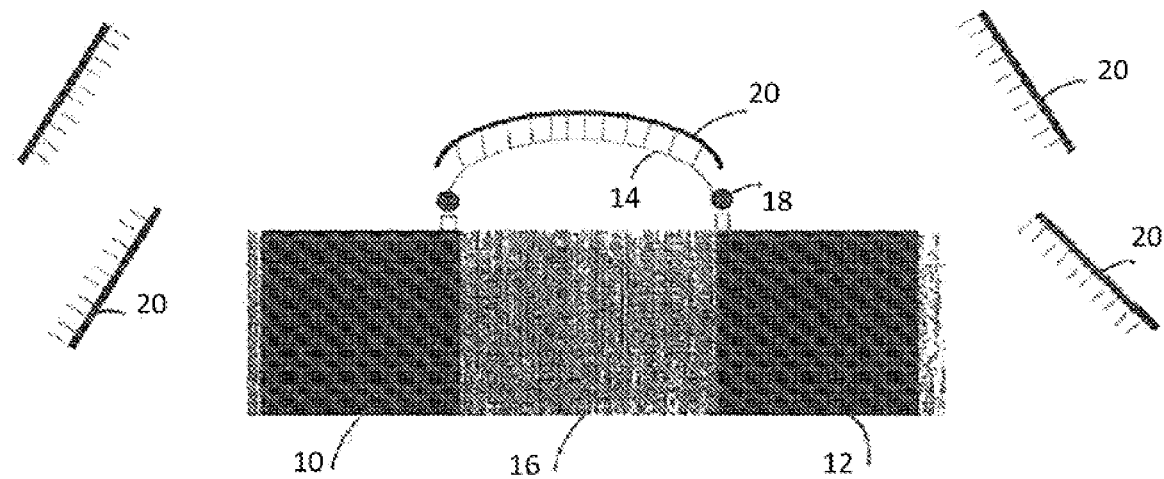
FIG. 1 illustrates a bridged electrode pair according to the prior art.
Figure 2:
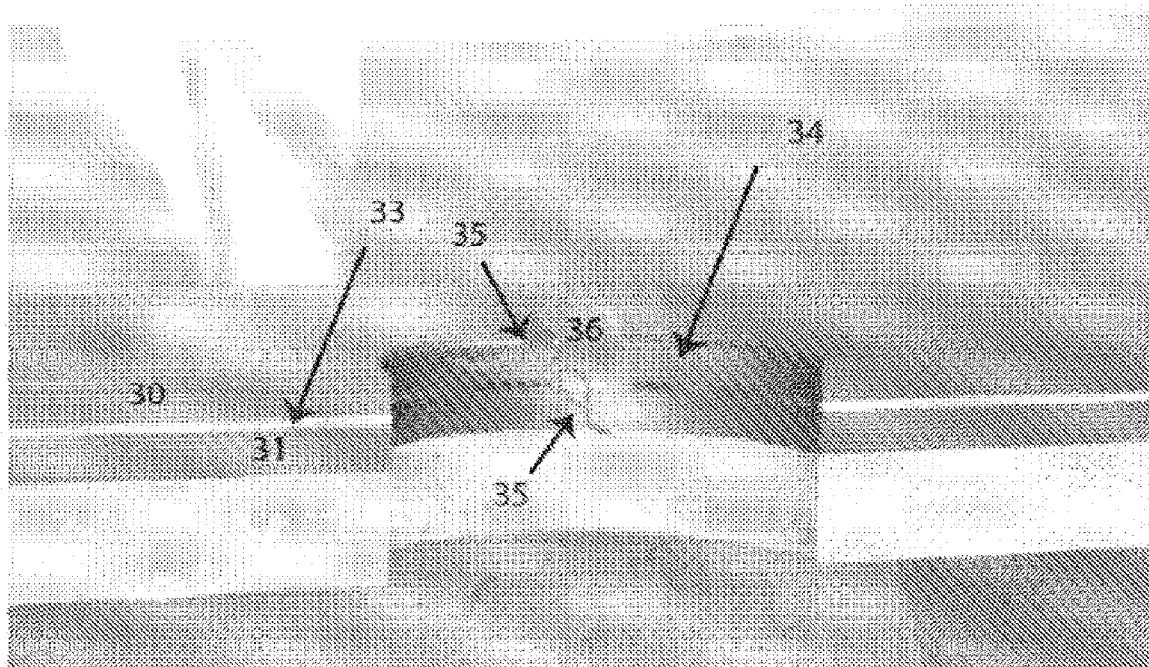
FIG. 2 illustrates a bridged electrode pair within a nanopore according to the prior art.

A single molecule sensing or detecting device includes a first electrode and a second electrode separated from the first electrode by a gap. The first electrode and the second electrode have an opening formed therethrough. At least one of the first electrode and the second electrode is functionalized with a recognition molecule. The recognition molecule has an effective length L1 and is configured to selectively bind to a target molecule having an effective length L2. The size of the gap is configured to be greater than L2, but less than or equal to the sum of L1 and L2.

In some embodiments, the device further includes an insulating layer disposed in the gap, wherein a thickness of the insulating layer is less than or equal to the sum of L1 and L2. In some embodiments, the size of the gap is at least twice the effective length L1. In some embodiments, the size of the gap is equal to the sum of L1 and L2. In some embodiments, the size of the gap is between about 2 nm to about 15 nm. In some embodiments, the size of the gap is between about 2 nm to about 10 nm. In some embodiments, the size of the gap is between about 5 nm to about 15 nm. In some embodiments, the recognition molecule includes any suitable peptide such as, for example, a cyclic RGD peptide. In some embodiments, the size of the opening is between 0.1 nm and 100 microns in a linear dimension.

In some embodiments, the first electrode and/or the second electrode are configured to generate a current upon binding of the target molecule and the current includes a fluctuating portion and/or a background portion. In some embodiments, the background portion of the current is based on a number of non-target molecules adsorbed on the first electrode and/or on the second electrode. In some embodiments, the fluctuating portion is based on a concentration of the target molecule in a solution containing the target molecule, the solution in contact with the first electrode and the second electrode, and the concentration of the target molecule in the solution is from about 10 fM to about 1 μM.

In some embodiments, a method for sensing or detecting a target molecule includes applying a voltage bias across a first electrode and a second electrode of a molecular sensing or detecting device. The first electrode and second electrode collectively have an opening formed therethrough. The second electrode separated from the first electrode by a gap, and at least one of the first electrode and the second electrode is functionalized with a recognition molecule. The recognition molecule includes an effective length L1 and is configured to selectively bind to a target molecule having an effective length L2. The method also includes contacting the first electrode and the second electrode with a solution containing the target molecule in a concentration from about 10 fM to about 1 μM. The method also includes monitoring current generated between the first electrode and the second electrode over time. The method also includes determining one or more of: the presence of the target molecule; and a number of non-target molecules adsorbed on the first electrode and/or on the second electrode.

In some embodiments, determining the presence of the target molecule is based on a fluctuating portion of the current. In some embodiments, determining a number of non-target molecules adsorbed on the first electrode and/or on the second electrode is based on a background portion of the current. In some embodiments, the device further includes an insulating layer disposed in the gap, and a thickness of the insulating layer is less than or equal to the sum of L1 and L2. In some embodiments, the gap is at least twice the effective length L1 in thickness. In some embodiments, the size of the gap is equal to the sum of L1 and L2. In some embodiments, the size of the gap is between about 2 nm to about 15 nm. In some embodiments, the size of the gap is between about 2 nm to about 10 nm. In some embodiments, the size of the gap is between about 5 nm to about 15 nm. In some embodiments, the recognition molecule includes a peptide. In some embodiments, the peptide is a cyclic RGD peptide.

It is commonly assumed that proteins are excellent insulators. Direct measurements of the conductance of small peptides (i.e., short protein fragments) in their linear form shows that current decays very rapidly with an increase in the length (i.e., number of amino acid residues) of the peptide (Xiao, Xu et al. 2004). However, scanning-tunneling microscope studies of electron-transfer proteins (Ulstrup 1979, Artes, Diez-Perez et al. 2012), can show remarkably large conductance values. While these values are impossible to reconcile with the short electronic decay lengths measured in peptides, it has recently been suggested that many proteins, in their three dimensional, folded form, are poised in a critical state between being a bulk conductor (metal-like) and an insulator, such that local fluctuations can drive proteins into states that are transiently conductive (Vattay, Salahub et al. 2015). Accordingly, some embodiments of the present disclosure are disclosed which enable proteins to form highly conductive bridges across gaps between electrodes that are much larger than could possibly support electron tunneling currents. Even with the most favorable electronic properties of a molecule in a tunnel junction, tunnel conductances drop below femtosiemens for distances of 3 to 4 nm Such large gaps provide, in at least some embodiments, a large current signal, even when the target protein is bound to only one electrode by a recognition reagent, with currents corresponding to nanosiemens of conductance.

EXAMPLE

Figure 3:
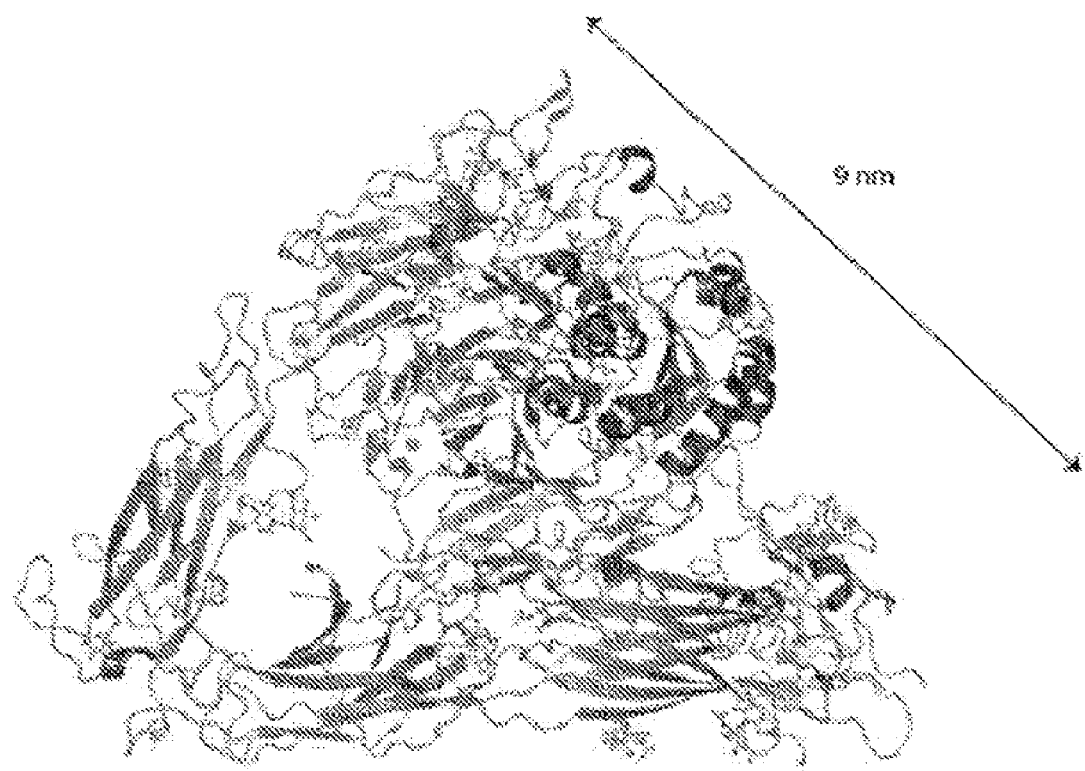
FIG. 3 illustrates a model of $\alpha v \beta_3$ integrin.
Figure 4A:
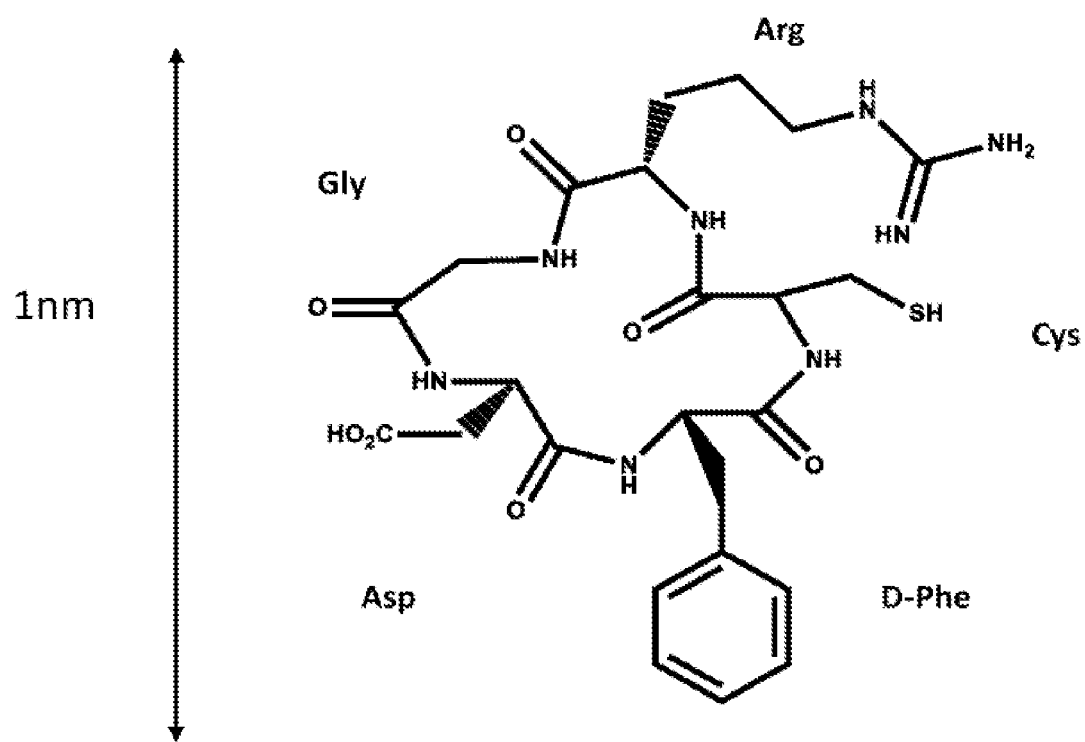
FIGS. 4a-4b illustrate (4a) Cyclic RGD peptide. (4b) Binding site of RGD peptide at the junction of the $\alpha$ and $\beta$ subunits of integrin.
Figure 4B:
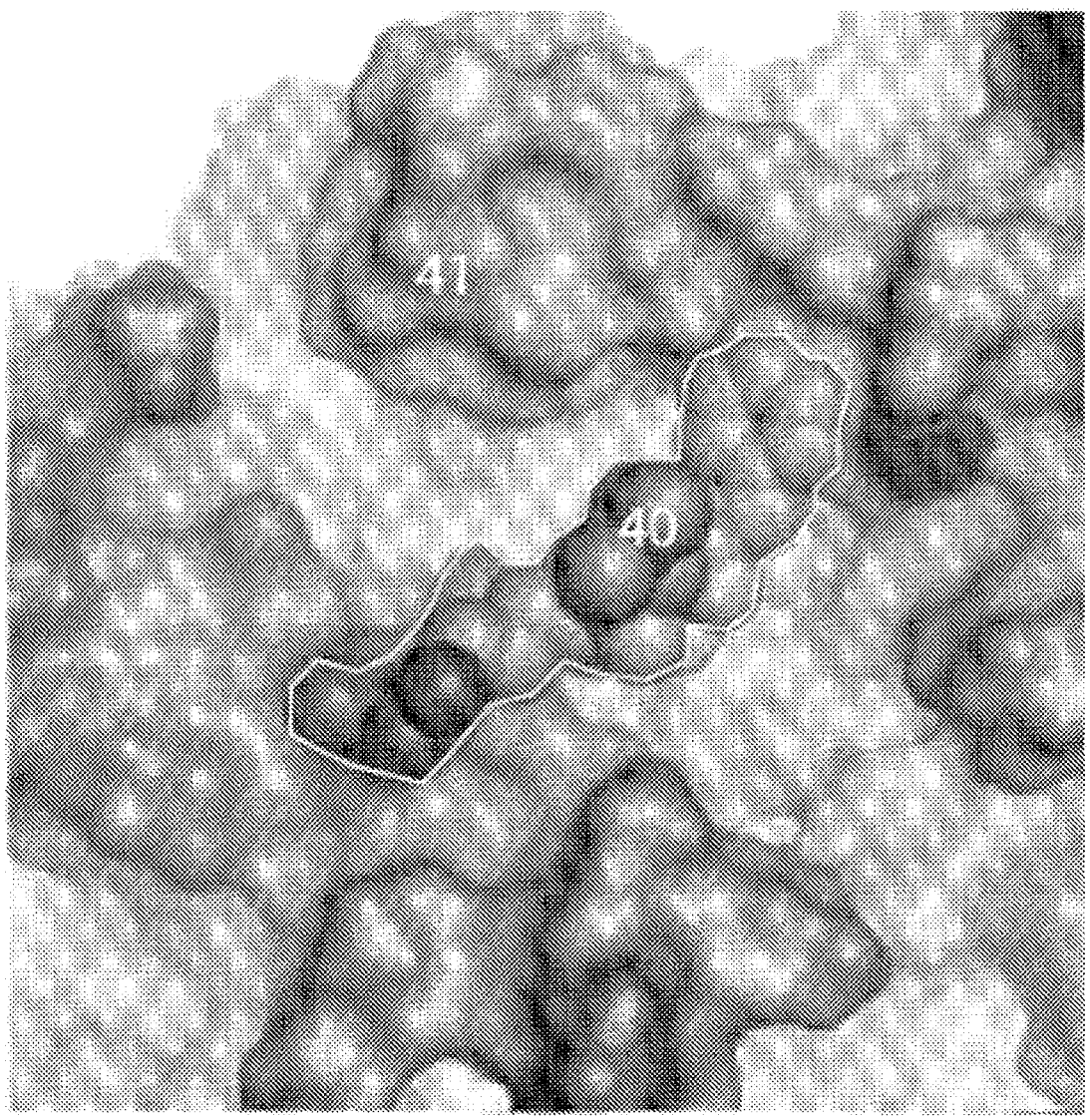

To illustrate the process we use the example of $\alpha v \beta_3$ integrin, which comprises two subunits (the $\alpha$ and $\beta$ chains) that meet at the apex of pyramidal shape that is about (in some embodiments) 9 nm high (FIG. 3). This protein is strongly bound by a cyclic RGB peptide (FIG. 4a) at a unique site near the apex of the pyramidal shape (FIG. 4b). In FIG. 4b, 41 is the junction between the $\alpha$ and $\beta$ chains and 40 is the cyclic RGD peptide (Choi, Kim et al. 2010). The peptide is relatively small being about 1 nm across its widest folded dimension.

Figure 5A:
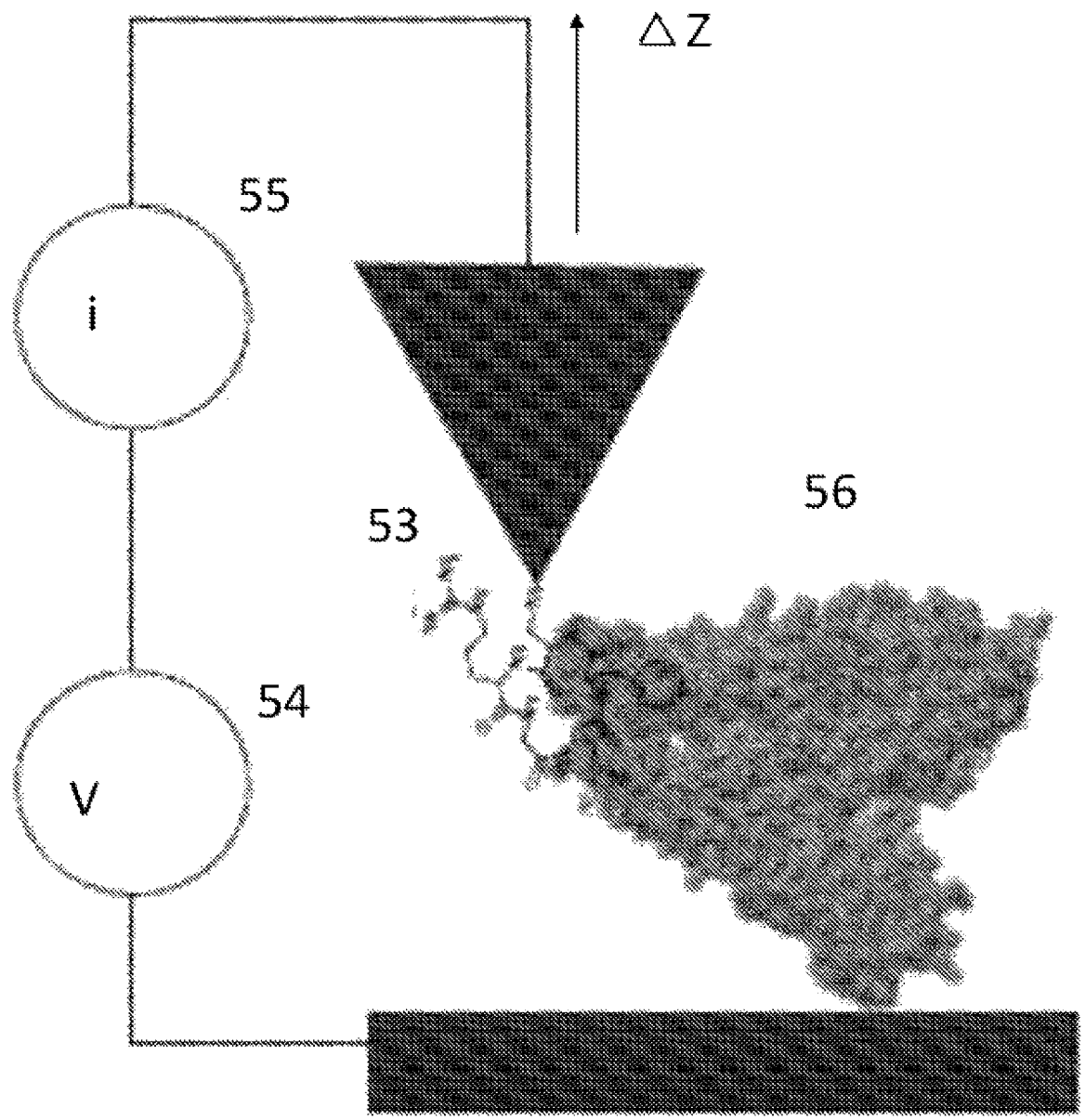
FIGS. 5a-5b illustrate scanning tunneling microscope experiment to demonstrate capture of $\alpha v \beta_3$ integrin with functionalization of just one electrode (FIG. 5a) and a typical current trace when an integrin is captured as the probe is withdrawn (FIG. 5b).
Figure 5B:
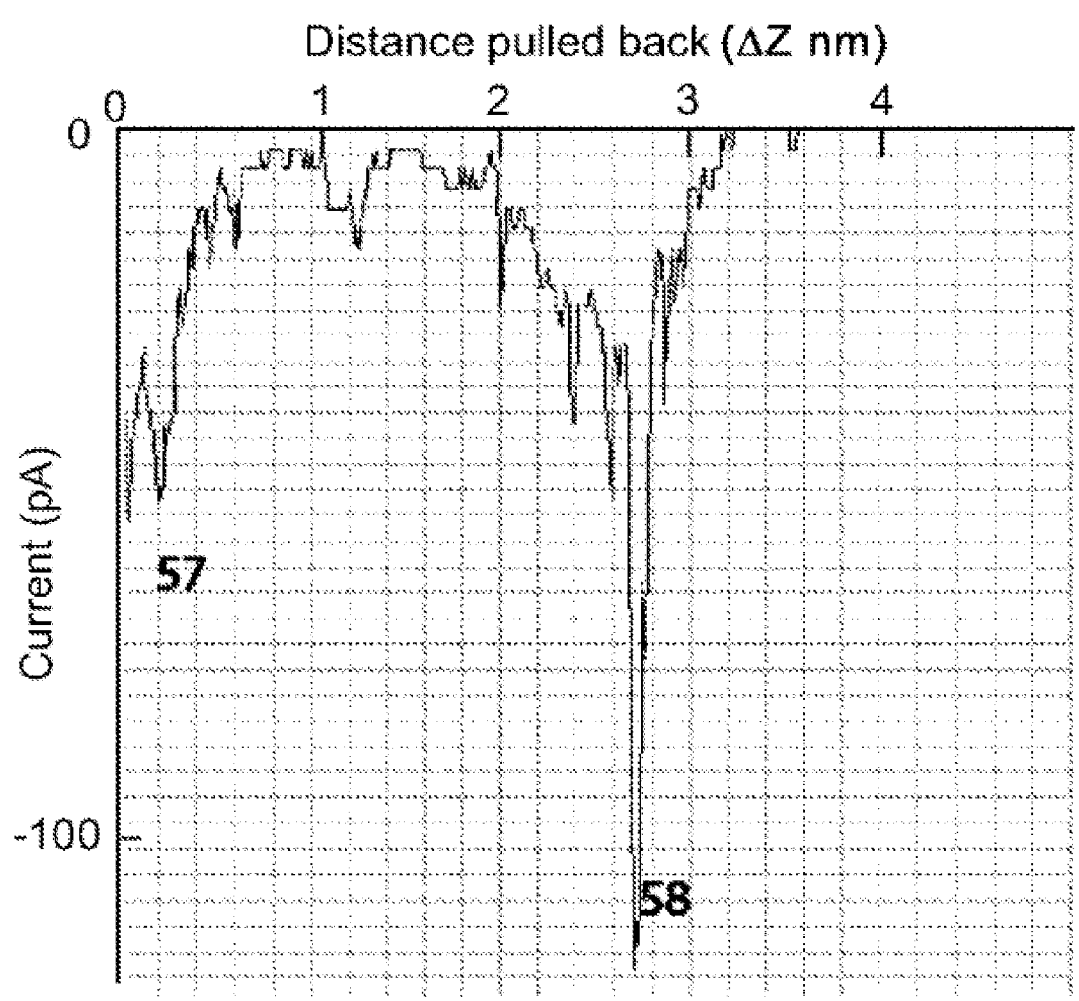

Accordingly, in some embodiments, functionalizing just one of a pair of electrodes generates a unique electrical recognition signal for a corresponding molecule(s). To do this, a scanning tunneling microscope (STM) was used (see STM, FIG. 5a), where a gold probe 51 was functionalized with the RGD peptide 53 via the chemical interaction between the cysteine residue and the gold. The probe was positioned at a set point bias (V) and current (I) such that the apex of the probe was held approximately 2.7 nm above a bare gold substrate, 52. As the probe was pulled away an extra distance $\Delta Z$, from the surface, a decaying current could be observed during some of the experiments (e.g., feature 57 in FIG. 5b). However, in the absence of the $\alpha v \beta_3$ integrin, no other features were observed, even if fairly high concentrations (e.g., 100 nM) of a protein such as BSA were added to the solution in the STM. Once 100 nM $\alpha v \beta_3$ integrin 56 was added to the solution, a new feature appeared as a current peak away from the origin 58 in FIG. 5b.

Figure 6A:
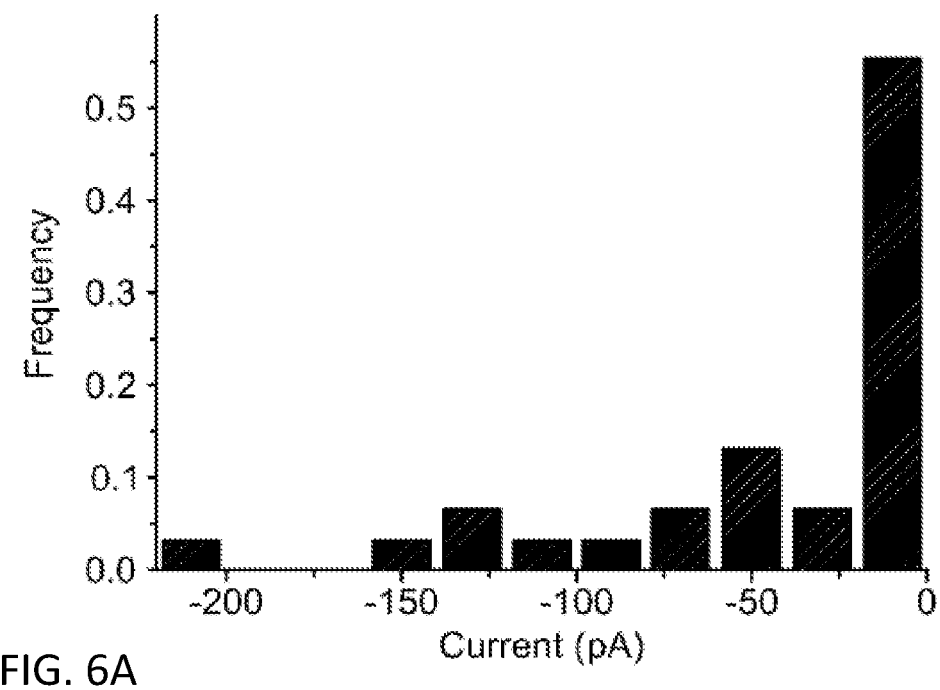
FIGS. 6a-6b illustrate a histogram of current peak values for integrin capture (FIG. 6a, current is shown increasing negative to the left here) and distribution of withdrawal distances to the peak signal (FIG. 6b, the starting gap, 0 on this plot, is 2.7 nm).
Figure 6B:
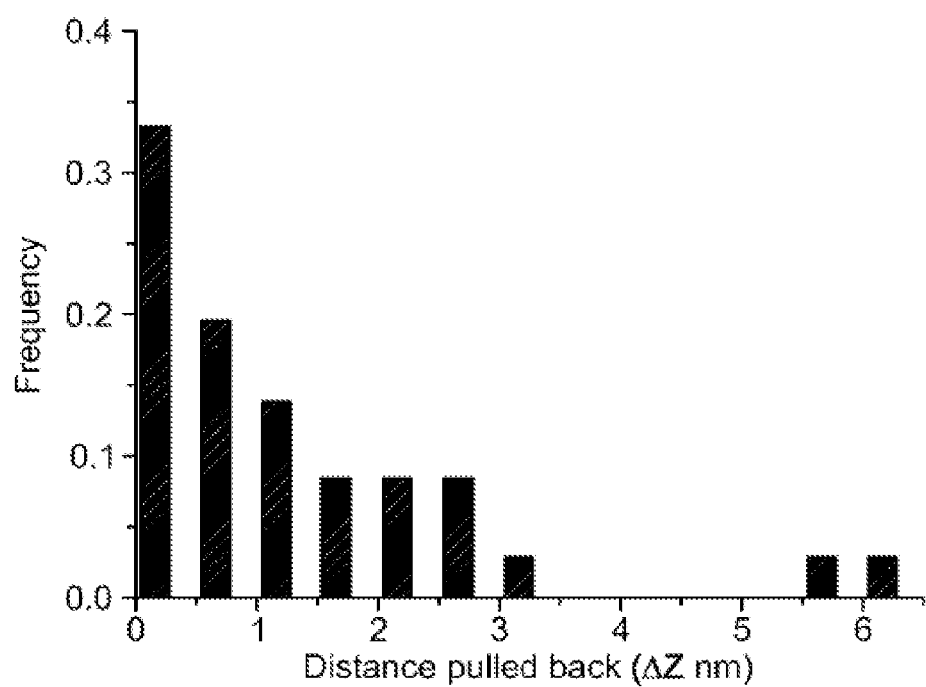

A statistical analysis of the distribution of features in terms of the peak current (FIG. 6a) and distance above approximately 2 nm for which a peak occurs ($\Delta Z$ in FIG. 6b) shows that signals of many tens of picoamps are generated at distances of about 3 nm to about 6 nm overall (2.7 nm+$\Delta Z$). In contrast to conventional tunneling signals, these signals peak when the probe is some distance away from the surface, signifying that the probe has captured a conductive particle. Importantly, no such features were seen in the absence of the $\alpha v \beta_3$ integrin, or in the presence of a protein (BSA) that does not bind the cyclic RGD peptide.

Figure 7:
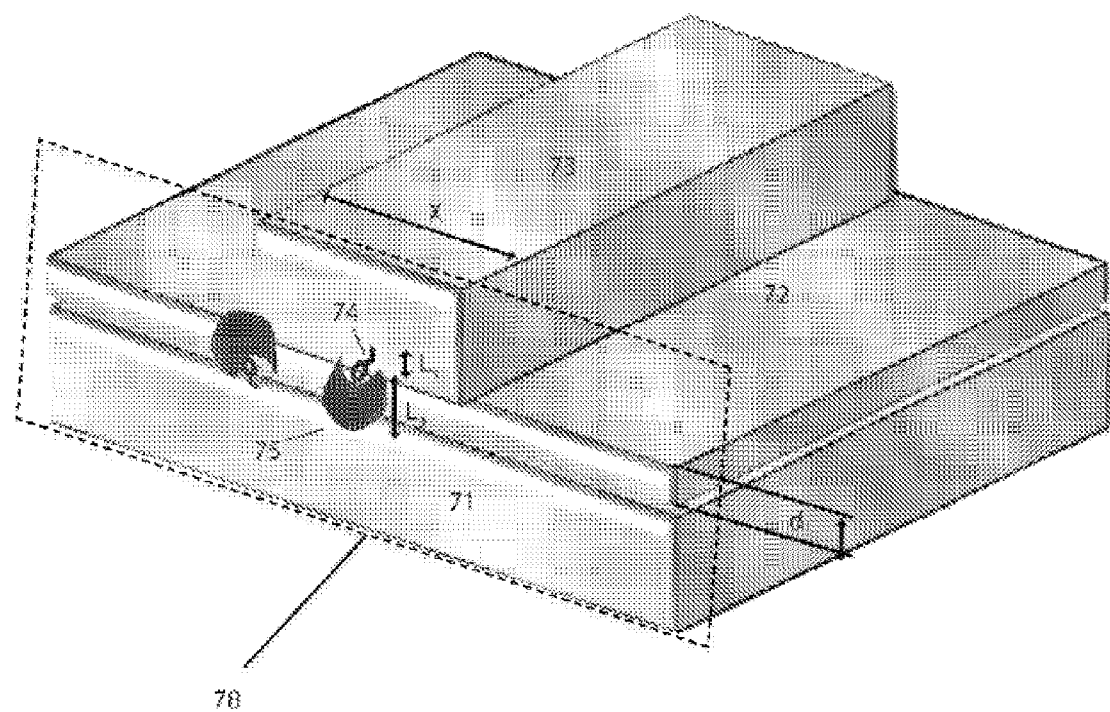
FIG. 7 illustrates a cross-sectional view of a tunnel junction edge of a device as exposed by an opening, according to some embodiments of the present disclosure.

FIG. 7 illustrates a cross-sectional view of a tunnel junction edge (i.e., the edge of an opening) of the device according to some embodiments of the present disclosure which includes a first metal electrode 71 (e.g., palladium, gold and/or platinum) onto which is deposited a layer of an insulating dielectric such as alumina 72 (for example). A second metal electrode 73 is then deposited, typically using one of the metals used for the first electrode. In some embodiments (not shown), the first electrode 71 and the second electrode 73 A cut is then made in the structure to expose the edge of these layers (fabrication of this type of device is described in detail in co-pending, published WO2015/161119, and also in Pang, Ashcroft et al. 2014) to form the opening/nanopore 78, shown here as a plane adjacent to the electrodes 71, 73. Accordingly, the first electrode 71 and the second electrode 73 can have an opening formed therethrough such as, for example, a nanopore. Said another way, the first electrode 71 and the second electrode 73 can be said to be arranged within or adjacent to an opening, or have a nanopore formed therethrough.

Figure 8:
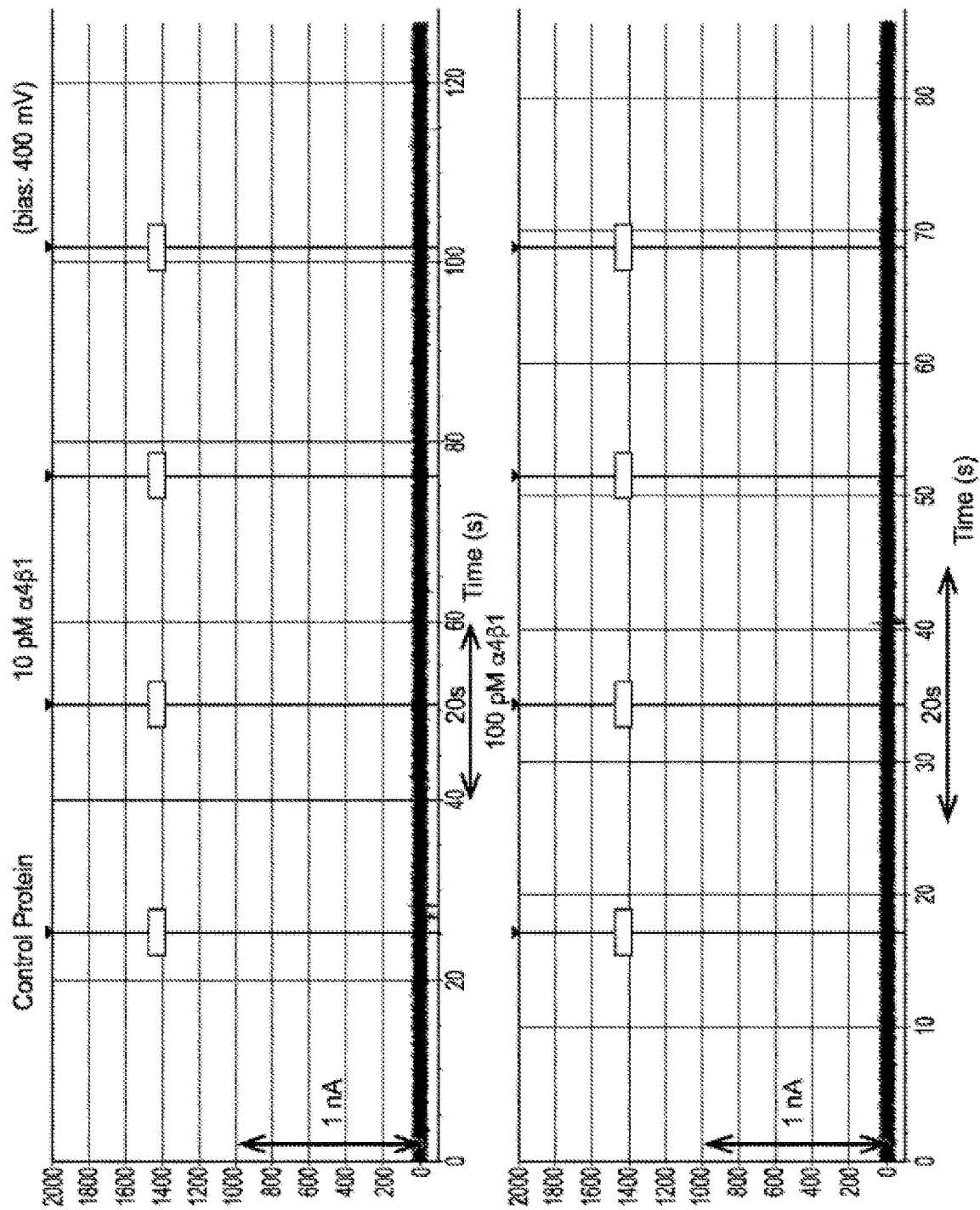
FIG. 8 illustrates current data recorded for two concentrations of $\alpha_4 \beta_1$ integrin, a molecule not bound by the RGD peptide with a device according to some embodiments.

In some such embodiments (of those illustrated in, e.g., FIG. 7), it is a particular feature of such embodiments in the use of, depending upon the embodiments, either or both of (a) recognition molecules that bind a target at only one site, so that the geometric constraints of forming a chemical bridge do not apply, and (b) a choice of dimensions that gives a very high signal-to-background ratio. Specifically, for example, the insulating layer 72 is deposited with a thickness d that is chosen to be greater than the longest linear dimension of the recognition molecules 74 ($L_1$, referred to as its effective length). However, according to some embodiments, it is chosen to be less than the combined overall length of the largest dimension of a target molecule 75 ($L_2$, also referred to as its effective length) bound to the recognition molecule 74 ($L_1+L_2$). In the case of the integrin-RGD pair (FIGS. 3 and 4) the RGD molecule is about 1 nm at its longest, while the integrin is 9 nm, for a total of about 10 nm This is a distance over which electron tunneling currents generally do not flow because the tunneling probability would be infinitesimal. However, a large particle that fluctuates into a highly conductive state could be used to mediate current flow (Vattay, Salahub et al. 2015). In some embodiments, the gap need only be made substantially larger than twice the largest dimension of the recognition molecules (i.e., >2$L_1$). Thus, for example, if a recognition molecule is 1 nm at its longest dimension, then the gap is configured to be greater than 2 nm, preferably by about 10%, to accommodate variations in the junction geometry (larger than 2.2 nm in this example). In some embodiments, a gap size can be from the noted minimum up to the size of one recognition molecule plus the size of the target protein. For example, if the largest dimension of the protein is 9 nm, then the gap in this case can be as big 9 nm plus the size of one of the recognition molecules (1 nm in this example), thus, a gap of 10 nm In experiments, devices functionalized with the cyclic RGD peptide and fabricated with a gap d of 3.5 to 4 nm show no background current, which continues to be the case even when the junctions are exposed to a homologous protein ($\alpha_4\beta_1$ integrin) that does not bind the RGD peptide. FIG. 8 shows current-vs time traces for devices in contact with 10 pM (a) and 100 pM (b) solutions of $\alpha_4\beta_1$ integrin.

However, when the junctions are exposed to the target protein ($\alpha v\beta_3$ integrin) signals appear immediately. FIG. 9 shows (a) the signal in 1 mM phosphate buffer (pH 7.0) just before the addition of a 1 pM solution of $\alpha v\beta_3$ integrin in the same buffer solution (b). A clear signal is immediately generated which includes two (2) features as marked: a background current (of about 0.5 nA in this case) and noise spikes of 0.5 to 1 nA superimposed on top. On increasing the concentration of $\alpha v\beta_3$ integrin to 10 pM, the background current increases by nearly an order of magnitude (while the fluctuations remain generally constant).

Figures 9A, 9B, 9C:
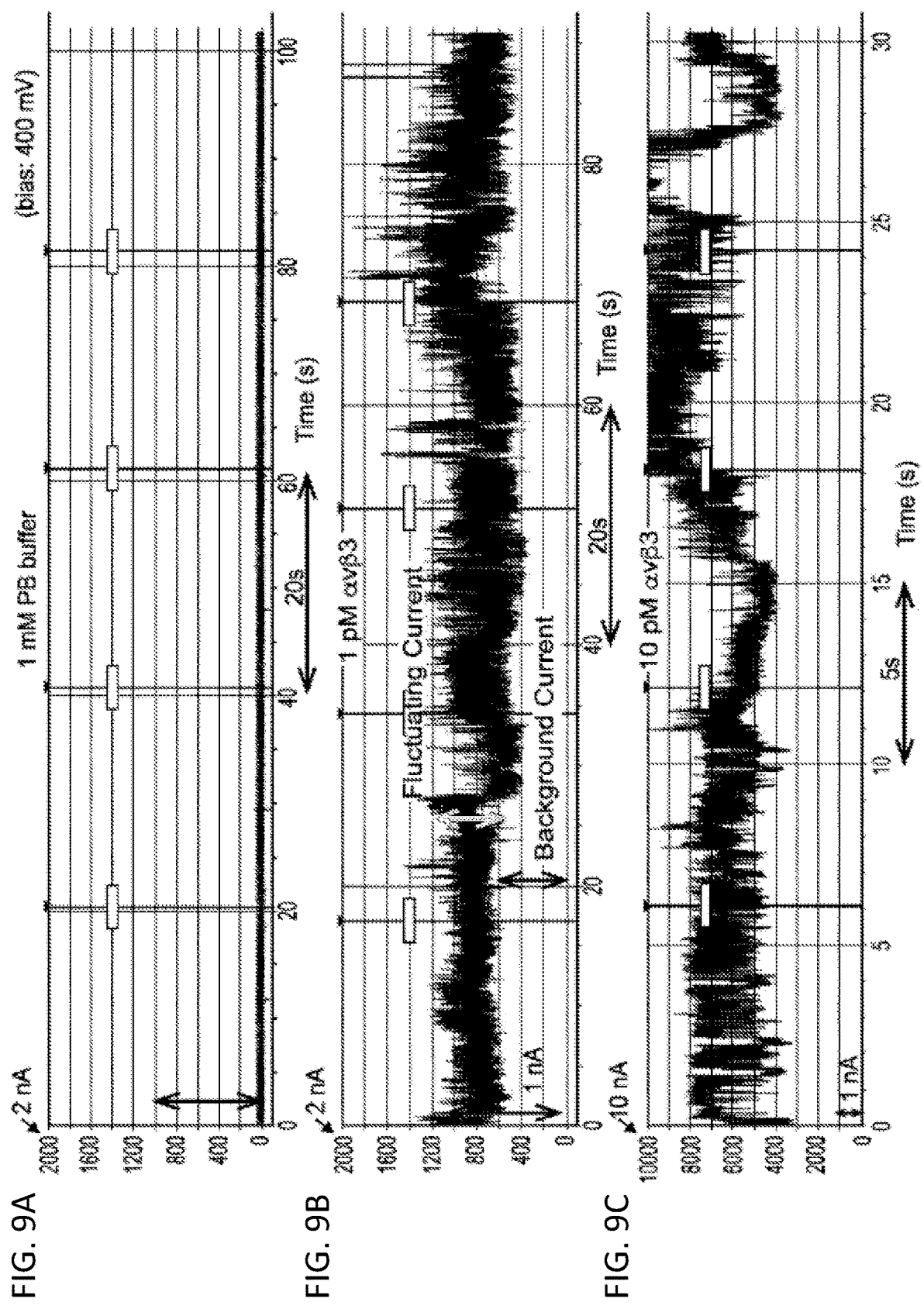
FIGS. 9a-9c illustrate current data from a device according to some embodiments, in buffer solution (9a) and then after adding 1 pM (9b), and then 10 pM (9c) of $\alpha v \beta_3$ integrin.
Figure 10A:
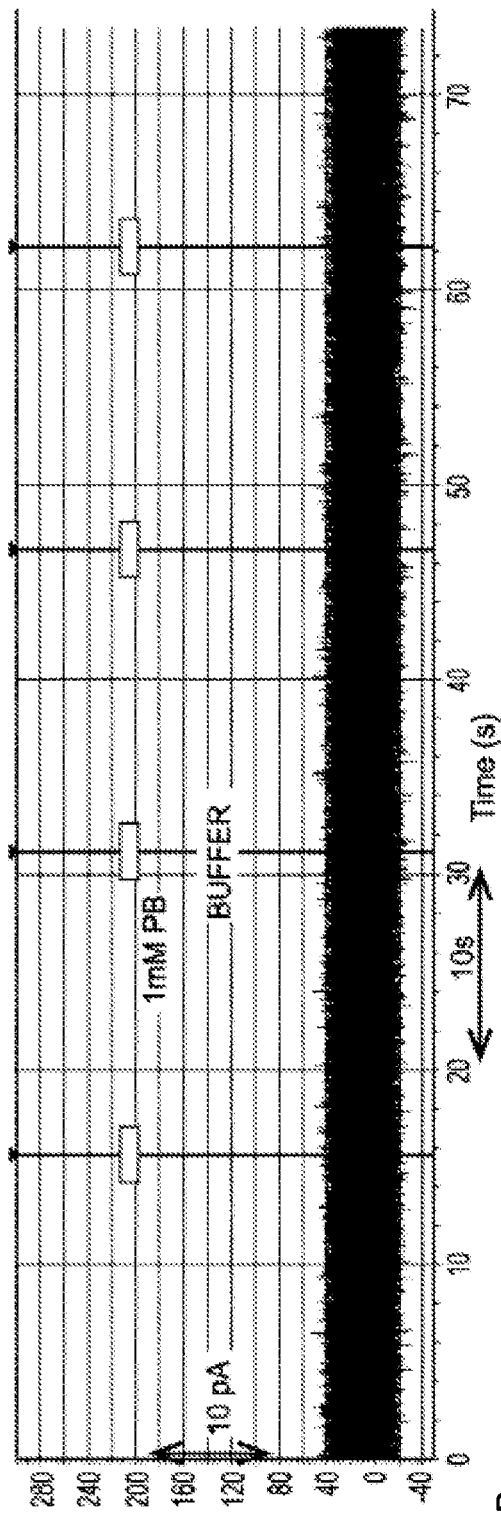
FIGS. 10a-10b illustrate control signals (10a, buffer, 10b, $\alpha_4 \beta_1$ integrin) for a nanopore device according to some embodiments of the present disclosure into which only a single molecule can be received.
Figure 10B:
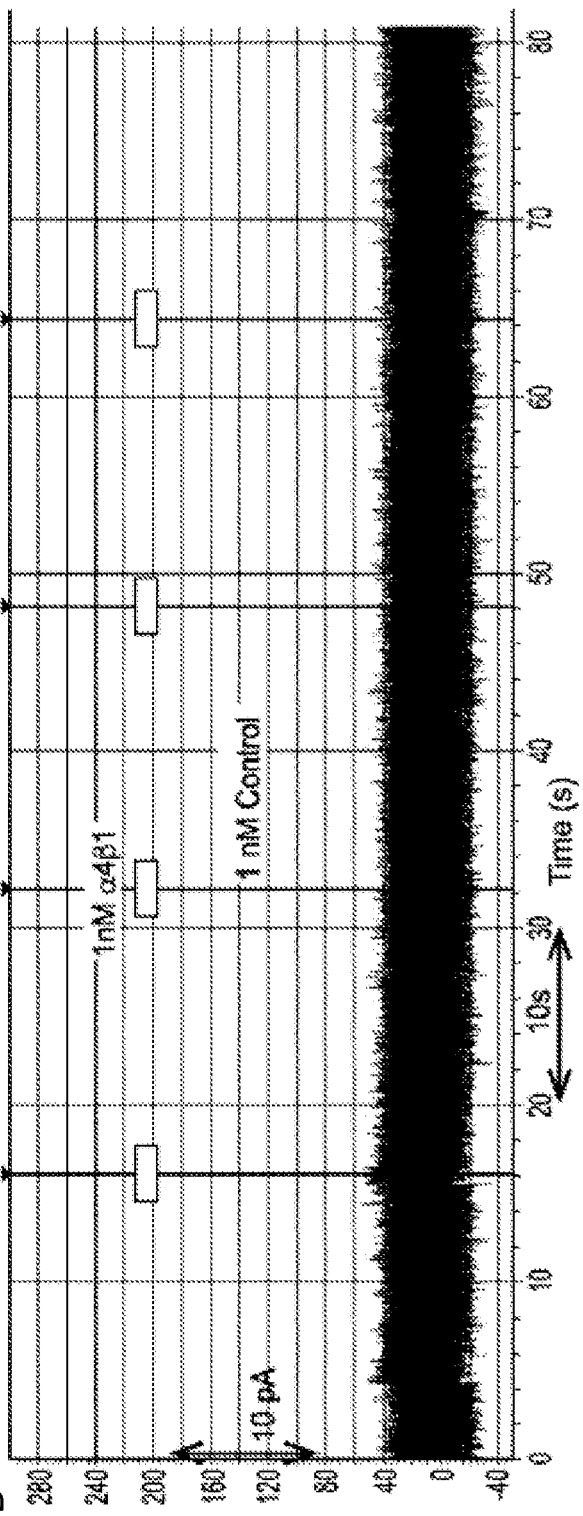
Figure 11:
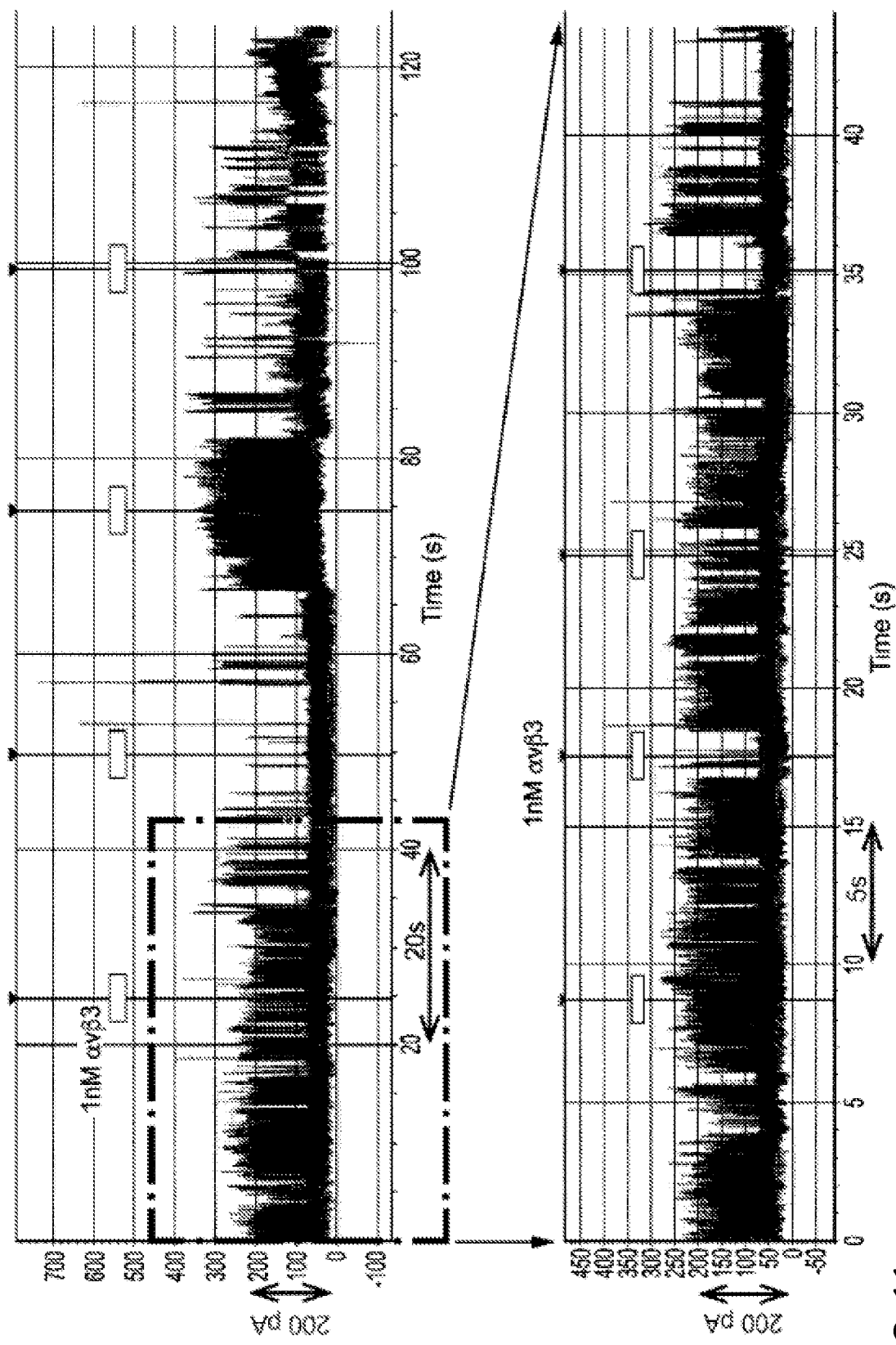
FIG. 11 illustrates a signal obtained when 1 nM $\alpha v \beta_3$ integrin was placed in contact with the nanopore device according to some embodiments of the disclosure.

Accordingly, in some embodiments, the background signal corresponds to the number of molecules adsorbed on the electrodes. This can be substantiated by collecting signals from a device small enough to allow only one integrin molecule to be trapped. In such a device, experiments were performed where the electrode edges were exposed by drilling a nanopore of approximately 12 nm diameter through the junction device. The electrodes were functionalized again with the cyclic RGD peptide. FIG. 10 shows that in phosphate buffer (a) or in the presence of a 1 nM solution of the non-binding control ($\alpha_4\beta_1$ integrin) no signals are generated. However, when 1 nM $\alpha v\beta_3$ integrin is added a signal is generated (FIG. 11). Note that even though the concentration of the protein is 100× that used to generate the signals shown in FIG. 9b, there is essentially no background current, only the fluctuating current component (of about 0.2 nA in this case). This is because there is room for only one molecule at a time in the device, and this confirms that, in some embodiments, the background current arises from adsorption of many molecules.

Figure 12:
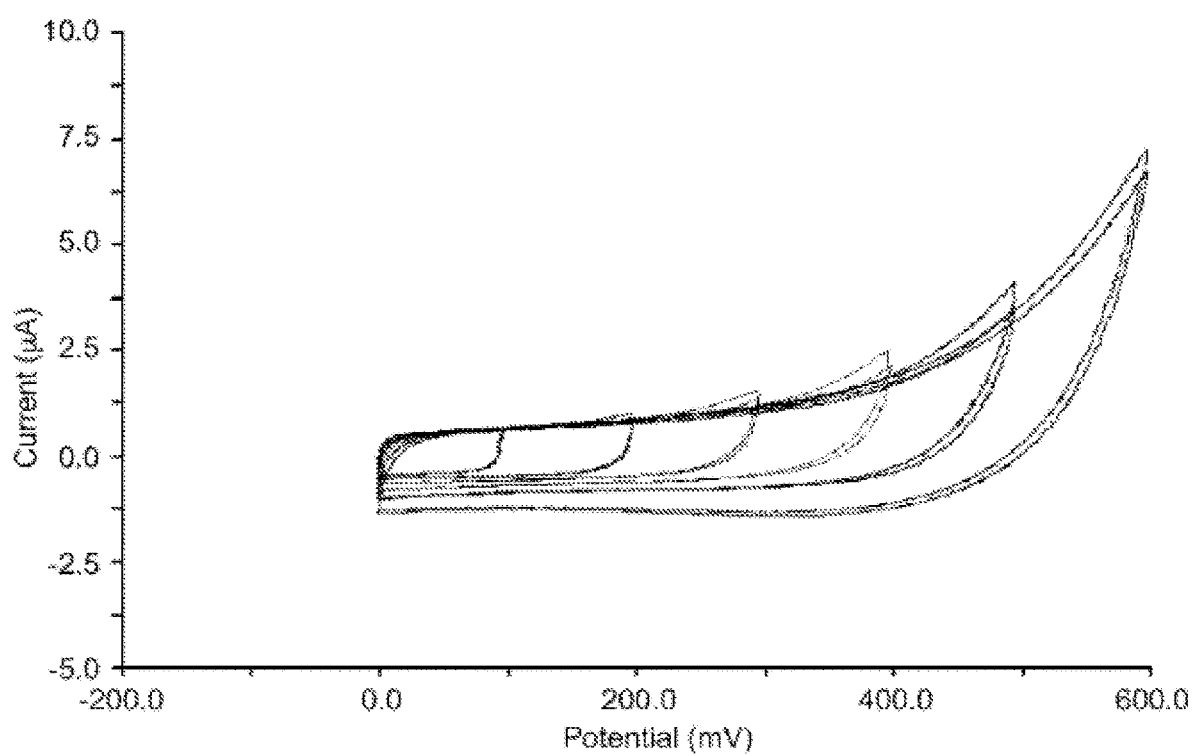
FIG. 12 illustrates cyclic voltammetry of a palladium electrode of a device according to some embodiments of the present disclosure functionalized with cyclic RGD peptide and exposed to a $\alpha v \beta_3$ integrin solution. Scale is millivolts relative to a silver wire quasi reference.

Stable operation of the device requires control of the operating potential as described for similar devices in PCT publication no. WO2015/130781, entitled, "Methods, Apparatuses and Systems for Stabilizing Nano-Electronic Devices in Contact with Solutions", the entire disclosure of which is herein incorporated by reference. FIG. 12 shows cyclic voltamograms taken with an RGD functionalized palladium electrode in the presence of a solution of $\alpha v\beta_3$ integrin. As shown, Faradaic current begins to rise above about 400 mV (with respect to a silver wire quasi reference electrode). Since, this is the upper limit of the bias applied to the across the electrode gap, the device operates stably if one electrode is connected to a silver wire (or Ag/AgCl) reference and the other electrode is kept below +400 mV with respect to the reference.

In experiments, the concentration used to obtain signals with the single molecule capture device had to be quite high (i.e., nanomolar or higher) in order for the probability of capturing a single molecule in a reasonable time to be significant. In some embodiments, this probability is proportional to the volume from which molecules can be captured in a reasonable time. For example, if the molecules diffuse freely with a diffusion constant D (e.g., about 10-11 m2/s), then the volume from which molecules can be collected in a time t, over a linear junction length L, is given approximately by $\pi r^2 L$ where $r^2 = Dt$. Taking t=60 s and L=36 nm (approximately the length of the junction around the edge of a 12 nm diameter pore), about 40 molecules would be present at 1 nM concentration in the resulting volume of $6.5 \times 10^{-17}$ m3 (=$6.5 \times 10^{14}$ liters). Referring to FIG. 7, if the junction length, X, is greatly increased (over the value of L given for the perimeter of a nanopore earlier, L=36 nm in the example given) then correspondingly, the sensitivity of the device will also increase. Thus, for a device with X=10 μm, the capture volume in 1 minute capture time becomes $10^{-14}$ m3 or almost 100× greater. Thus, signals are readily obtained at 1 pM concentrations as shown in FIG. 9b. In fact, upon the solution being flowed over the device, the effective capture length is orders of magnitude greater. For the cyclic RGD peptide, capturing $\alpha v\beta_3$ integrin, the binding process appears to be almost irreversible, so essentially all of the molecules within a capture radius can be swept up. Thus, if about a linear cm of fluid is flowed past a junction slowly enough that each volume of length equal to the junction length spends about a minute over the junction, then concentrations as small as a femtomole will yield a signal.

Figure 13:
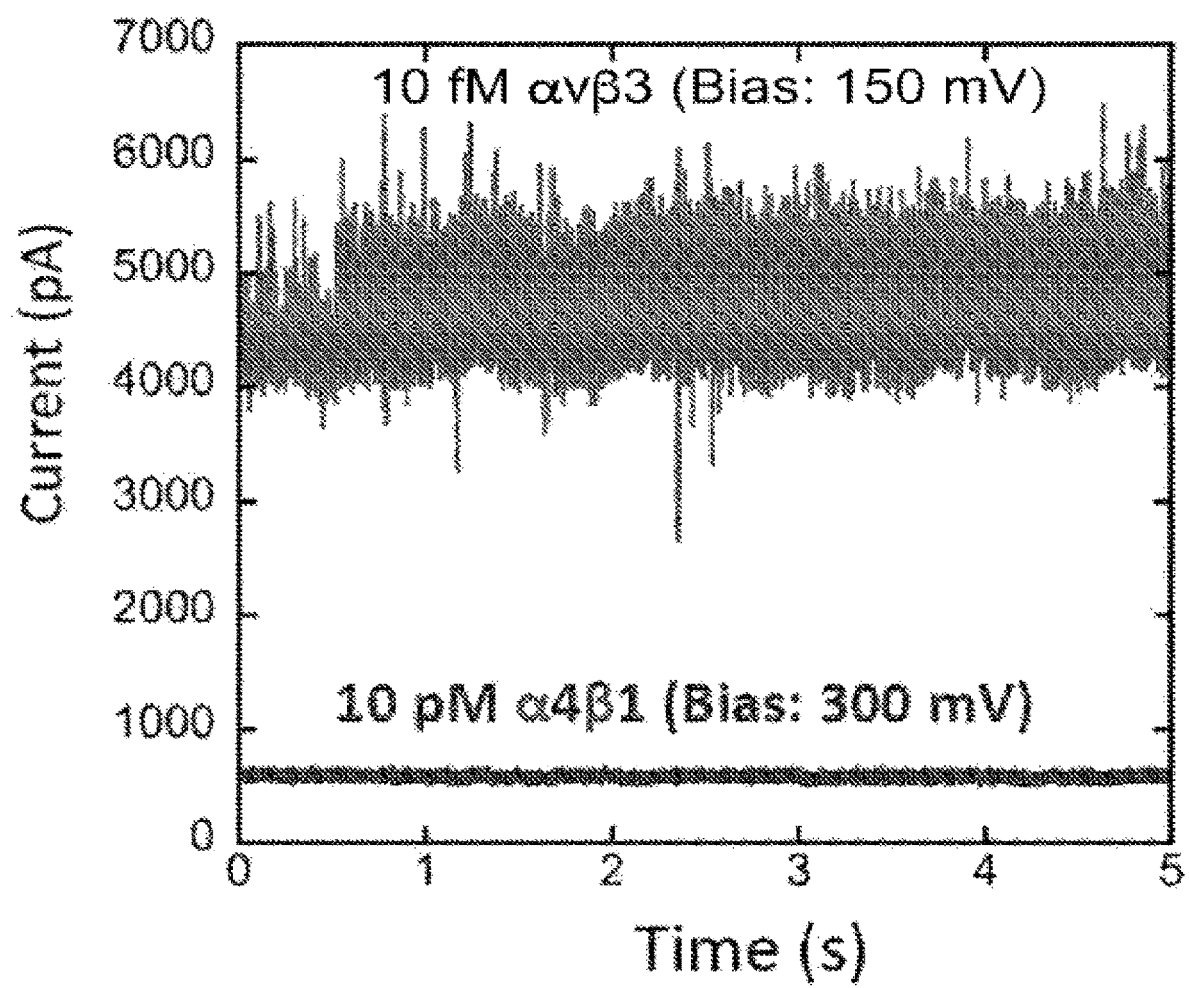
FIG. 13 illustrates output of a device according to some embodiments with a large (micron sized) junction length exposed to a 10 pM solution of $\alpha_4 \beta_1$ integrin (lower trace) followed by a 10 femtomolar solution of $\alpha v \beta_3$ integrin (upper trace).

FIG. 13 shows an experiment in which a 10 pM solution of $\alpha_4\beta_1$ integrin was flowed over large (X=0.1 μm junction) for several minutes with no signal being produced. When 10 fM of $\alpha v\beta_3$ integrin was introduced, a large signal appeared after a few minutes, which substantially exceeds the sensitivity estimated above (where much longer exposure times would be required for the even larger (X=10 μm) junction geometry.

One of skill in the art recognizes that the specific dimensions given here are exemplary only. For example, a much larger gap (e.g., 5 to 15 nm), can be used if the recognition molecules (cognate ligands) are full sized antibodies (e.g., about 10 nm in extent), so the gap size (d in FIG. 7) would be, for example, 20 nm. An alternative to antibodies could be single-domain antibodies such as those produced by Abcore Inc. (for example). Such single-domain antibodies include molecular weights of 50 kD and linear dimensions of around 2.5 nm, so gaps of 5 nm would be appropriate.

Any and all references to publications or other documents, including but not limited to, patents, patent applications, articles, webpages, books, etc., presented anywhere in the present application, are herein incorporated by reference in their entirety.

As noted elsewhere, the disclosed embodiments have been presented for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, compositions, systems and apparatuses/devices which may further include any and all elements from any other disclosed methods, compositions, systems, and devices, including any and all elements corresponding to detecting one or more target molecules (e.g., DNA, proteins, and/or components thereof). In other words, elements from one or another disclosed embodiments may be interchangeable with elements from other disclosed embodiments. Moreover, some further embodiments may be realized by combining one and/or another feature disclosed herein with methods, compositions, systems and devices, and one or more features thereof, disclosed in materials incorporated by reference. In addition, one or more features/elements of disclosed embodiments may be removed and still result in patentable subject matter (and thus, resulting in yet more embodiments of the subject disclosure). Furthermore, some embodiments correspond to methods, compositions, systems, and devices which specifically lack one and/or another element, structure, and/or steps (as applicable), as compared to teachings of the prior art, and therefore represent patentable subject matter and are distinguishable therefrom (i.e. claims directed to such embodiments may contain negative limitations to note the lack of one or more features prior art teachings).

Also, while some of the embodiments disclosed are directed to detection of a protein molecule, within the scope of some of the embodiments of the disclosure is the ability to detect other types of molecules.

When describing the molecular detecting methods, systems and devices, terms such as linked, bound, connect, attach, interact, and so forth should be understood as referring to linkages that result in the joining of the elements being referred to, whether such joining is permanent or potentially reversible. These terms should not be read as requiring a specific bond type except as expressly stated.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

LITERATURE CITED

DEVICES AND METHODS FOR TARGET MOLECULE CHARACTERIZATION. US Application 2010/0084276 A1

DIGITAL PROTEIN SENSING CHIP AND METHODS FOR DETECTION OF LOW CONCENTRATIONS OF MOLECULES Application 61/980,317 filed Apr. 16, 2014

METHODS AND APPARATUSES AND SYSTEMS FOR STABILIZING NANO-ELECTRIC DEVICES IN CONTACT WITH SOLUTIONS application 61/944,322.

Artes, J. M., I. Diez-Perez and P. Gorostiza (2012). "Transistor-like behavior of single metalloprotein junctions." *Nano Lett* 12(6): 2679-2684.

Choi, Y., E. Kim, Y. Lee, M. H. Han and I. C. Kong (2010). "Site-specific inhibition of integrin alpha v beta 3-vitronectin association by a ser-asp-val sequence through an Arg-GlyAsp-binding site of the integrin." *Proteomics* 10(1): 72-80.

Cui, X. D., A Primak, X. Zarate, J. Tomfohr, O. F. Sankey, A. L. Moore, T. A Moore, D. Gust, G. Harris and S. M. Lindsay (2001). "Reproducible measurement of single-molecule conductivity." *Science,* 294: 571-574.

Pang, P., B. Ashcroft, W. Song, P. Zhang, S. Biswas, Q. Qing, J. Yang, R. J. Nemanich, J. Bai, J. Smith, K. Reuter, V. S. K. Balagurusamy, Y. Astier4, G. Stolovitzky and S. Lindsay (2014). "Fixed Gap Tunnel Junction for Reading DNA Nucleotides." ACS Nano 8: 11994 12003.

Pishrody, S. M., S. Kunwar and G. T. Mathai (2004). Electronic Detection of Biological Molcules using thin layers, U.S. Pat. No. 6,824,974 B2 Nov. 30, 2004.

Ulstrup, J. (1979). *Charge transfer processes in condensed media*. Berlin, Springer-Verlag.

Vattay, G., D. Salahub, I. Csabai, A Nassimi and S. A Kaufmann (2015). "Quantum Criticality at the Origin of Life." arXiv:1502.06880 [cond-mat.dis-nn].

Xiao, X., B. Xu and N. Tao (2004). "Conductance Titration of Single-Peptide Molecules." *J. Am Chem Soc* 126: 5370-5371.

Zwolak, M. and M. Di Ventra (2005). "Electronic Signature of DNA Nucleotides via Transverse Transport." Nano Lett. 5: 421-424.

What is claimed is:

1. A sensing device for sensing target molecule fluctuations, comprising:
   a first electrode and a second electrode separated from the first electrode by a gap; and
   at least one recognition molecule comprising a first end with a first chemical composition to bind the first electrode or the second electrode, and a second end with a second chemical composition to bind the target molecule;
   wherein the gap is bridged by the target molecule bound by the at least one recognition molecule, thereby completing an electrical circuit.

2. The sensing device of claim 1, wherein the at least one recognition molecule has an effective length L1 and is configured to selectively bind to the target molecule having an effective length L2, and wherein the size of the gap is configured to be greater than L2.

3. The sensing device of claim 2, wherein the device comprises an insulating layer disposed in the gap, and wherein a thickness of the insulating layer is less than or equal to the sum of L1 and L2.

4. The sensing device of claim 2, wherein the size of the gap is at least twice the effective length L1.

5. The sensing device of claim 2, wherein the size of the gap is equal to the sum of L1 and L2.

6. The sensing device of claim 1, wherein the size of the gap is between about 2 mn to about 15 nm.

7. The sensing device of claim 1, wherein the size of the gap is between about 2 nm to about 10 nm.

8. The sensing device of claim 1, wherein the size of the gap is between about 5 nm to about 15 nm.

9. The sensing device of claim 1, wherein the at least one recognition molecule comprises a peptide.

10. The sensing device of claim 1, wherein the at least one recognition molecule comprises a cyclic RGD peptide.

11. The sensing device of claim 1, wherein the target molecule is a protein.

12. The sensing device of claim 1, wherein the first electrode and the second electrode are collectively configured to generate a current upon binding of the target molecule, the current including a fluctuating portion and a background portion.

13. The sensing device of claim 12, wherein the background portion of the current is based on a number of non-target molecules adsorbed on the first electrode and/or on the second electrode.

14. The sensing device of claim 12, wherein the fluctuating portion is based on a concentration of the target molecule in a solution containing the target molecule, wherein the solution is in contact with the first electrode and the second electrode, and wherein the concentration of the target molecule in the solution is from about 10 fM to about 1 μM.

15. The sensing device of claim 14, wherein one contact is made with the first electrode via the recognition molecule and a second contact is made with the second electrode at a second point, thereby forming a bridge.

16. The sensing device of claim 1, wherein the first electrode and second electrode are collectively configured so that a voltage bias can be applied across the gap and fluctuations of the target molecule recorded.

17. The sensing device of claim 1, wherein at least the first electrode or second electrode couples to a reference electrode.

* * * * *